United States Patent [19]

Rheinberger et al.

[11] Patent Number: 5,102,461

[45] Date of Patent: Apr. 7, 1992

[54] PROCESS FOR THE OPTICAL DISTINCTION OF A DENTAL MATERIAL AND DENTAL MATERIAL FOR SAID PROCESS

[75] Inventors: Volker Rheinberger, Vaduz, Liechtenstein; Ulrich Salz, Weissenberg, Fed. Rep. of Germany; Gilbert Ott, Nendeln, Liechtenstein

[73] Assignee: Ivoclar AG, Schaan, Fed. Rep. of Germany

[21] Appl. No.: 620,470

[22] Filed: Nov. 30, 1990

[30] Foreign Application Priority Data

Dec. 2, 1989 [DE] Fed. Rep. of Germany ....... 3939998

[51] Int. Cl.$^5$ ................................................. C09K 3/00
[52] U.S. Cl. ...................................................... 106/35
[58] Field of Search .......................................... 106/35

[56] References Cited

U.S. PATENT DOCUMENTS 3,960,753  6/1976  Larrabee .......................... 252/299.7
4,957,441  9/1990  Byran ................................ 433/228.1

Primary Examiner—William R. Dixon, Jr.
Assistant Examiner—Margaret V. Einsmann
Attorney, Agent, or Firm—Cushman, Darby & Cushman

[57] ABSTRACT

In a method for the optical distinction of a dental material applied to a substrate from natural teeth, false teeth or parts thereof 0.00001 to 1% by wt. of a fluorescent substance having an absorption maximum in the wave length range of 360 to 480 nm and a fluorescence maximum in the wave length range of 480 to 600 nm is incorporated in the dental material, the dental material is applied to the substrate and irradiated with a light source emitting light of a wave length in the region of 360 to 480 nm and is then viewed through a light filter filtering out at least partially the light of a wave length in the region of 360 to 480 nm.

4 Claims, No Drawings

PROCESS FOR THE OPTICAL DISTINCTION OF A DENTAL MATERIAL AND DENTAL MATERIAL FOR SAID PROCESS

The invention relates to a process for the optical distinction of a dental material applied to a substrate from natural teeth, false teeth or parts thereof, and to a dental material for use in this process.

Processes for the optical distinction of a dental material from natural teeth are known. Thus, a process is described in U.S. Pat. No. 4 600 389 in which fluorescent lanthanide compounds incorporated in microcapsules are added to dental materials and these dental materials are subsequently excited to fluorescence with the UV irradiation of a mercury vapor lamp with a wave length of 366 nm. The fluorescent light occurring during this process exhibits a red or green color depending on the nature of the lanthanide compound used, as a result of which there is said to be a sufficient distinguishing capacity with respect to the likewise occurring bluish-white fluorescence of natural teeth. The incorporation of the lanthanide compounds in microcapsules is necessary in order to ensure the compatibility thereof with different dental materials and moreover to prevent premature nonoccurrence of the fluorescent effect which would otherwise be brought about by chemical decomposition and/or washing out of the lanthanide compounds.

In published GB patent application 2 190 917, strongly colored protective films for teeth are described which, in addition to conventional dyes for increasing the distinguishing capacity with respect to the dental environment, can contain fluorescent pigments which are excited to fluorescence with light having wave length of 400 to 600 nm. The protective films are intended to remain only for a short period on the tooth where they act as a high-contrast background for a subsequent filling of cavities with tooth-colored filling material.

In the case of both the processes listed above, however, the interfering effects attributable to the strong inherent fluorescence of natural teeth are left out of consideration. Thus even the small proportions of near UV light of daylight are sufficient to excite the natural tooth to fluorescence. A reliable distinction of the fluorescent dental material from the natural teeth is thereby made more difficult according to the known processes. In addition to the bluish-white fluorescence of natural teetch, the blue light with a wave length of 400 to 600 nm used to excite fluorescence according to published patent specification GB 2 190 917 represents a source of interference which impedes the simple distinction of the dental material and the surrounding natural teeth.

Consequently, it is an object of the invention to provide a process for the optical distinction of a dental material applied to a substrate from natural teeth, false teeth or parts thereof, in which the dental material undergoes essentially no visible color change due to the incorporation of the fluorescent substances, the fluorescent substances are compatible with different dental materials even without being incorporated in microcapsules and are stable towards chemical and physcial effects, and in which the interfering effects caused by the inherent fluorescence of the natural teeth and by the exciting blue light are essentially excluded, and a dental material for use in this process.

This technical problem is solved by a process for the optical distinction of a dental material applied to a substrate from natural teeth, false teeth or parts thereof in which 0.00001 to 1% by wt. of a fluorescent substance having an absorption maximum in the wave length range of 360 to 480 nm and a fluorescence maximum in the wave length range of 480 to 600 nm is incorporated in the dental material, the dental material applied to the substrate is irradiated with a light source which emits light with a wave length in the region of 360 to 480 nm and is viewed through a light filter filtering out at least partially the light with a wave length in the region of 360 to 480 nm.

The fluorescent substances incorporated in the dental material in a quantity of 0.00001 to 1% by wt., preferably 0.001 to 0.1% by wt. in the process according to the invention have an absorption maximum in the wave length range of 360 to 480 nm and a fluorescence maximum in the wave length range of 480 to 600 nm.

Preferred fluorescent substances are coumarin derivatives, phthalimide derivatives, fluoranthene derivatives, perylene derivatives, xanthene derivatives, thioxanthene derivatives, pyrano-benzopyran-2,5-dione derivatives, pyrano-quinoline-2,5 derivatives, pyrazole quinoxaline derivatives, 2-pyrano-isoquinoline-3,6-dione derivatives, benzimidazo-benz-isoquinoline-7-one derivatives, acridine derivatives and mixtures of the above mentioned derivatives. The following, for example, are particularly preferred coumarin derivatives:

7-(dimethylamino)-4-(trifluoromethyl) coumarin, 7-amino-4-(trifluoromethyl) coumarin, 7-(dimethylamino)-4-(trifluoromethyl) coumarin, 7-(ethylamino)-6-methyl-4-(trifluoromethyl) coumarin, 2,3,6,7-tetrahydro-9-(trifluoromethyl-1H,5H,11H-[1] benzopyrano [6,7,8-ij]-quinolizine-11-one, 6,7,8,9-tetrahydro-4-(trifluoromethyl)-2H-pyrano [3,2,-c] quinoline-2-one, 7-(diethylamino)-3-(1-methyl-1H-benzimidazol-2-yl)-2H-1-benzopyran-2-one, 3-(2-benzimidazolyl)-7-(diethylamino) coumarin, 10-acetyl-2,3,6,7-tetrahydro-1H,5H,11H-[1] benzopyrano [6,7,8-ij] quinolizine-11-one, 3-(2-benzothiazolyl)-7-(diethylamino) coumarin, 2,3,6,7-tetrahydro-11-oxo-1H,5H,11H-[1] benzopyrano [6,7,8-ij] quinolizine-10-carboxylic acid and 2,3,6,7-tetrahydro-11-oxo-1H,5H,11H-[1] benzopyrano [6,7,8-ij] quinolizine-10-ethyl carboxylate.

Preferred phthalimide derivatives are e.g. 4-amino-N-methyl phthalimide, 4-(dimethylamino)-N-methyl phthalimide and 4-(2H-naphthol[1,2-d]triazol-2-yl)-N-methyl phthalimide.

Suitable fluoranthene derivatives are e.g. fluoranthene-2,3-dicarboxylic anhydride and 1-methyl fluoranthene-2,3-dicarboxylic anhydride.

Representative perylene derivatives are e.g. perylene and 3,9-perylene diisobutyl dicarboxylate.

Preferred xanthene derivatives are e.g. 2,8-dimethyl-naphtho-[3,2,1-k]xanthene.

As thioxanthene derivatives e.g. benzothioxanthene-3,4-dicarboxylic acid-N-stearylimide, and as pyrano-benzopyran-2,5-dione derivatives e.g. 3-(benzothiazol-2-yl)2H,5H-pyrano[3,2,c][1]benzopyran-2,5-dione, 3-(benzimidazol-2-yl)-2H,5H-pyrano[3,2,c][1]benzopyran-2,5-dione, 8-hydroxy-3-(benzimidazol-2-yl)-2H,5H-pyrano-[3,2,c[1]benzopyran-2,5-dione, 8-(dimethylamino)-3-phenyl-2H,5H-pyrano[3,2,c][1]benzopyran-2,5-dione, 8-(dimethylamino)-3-(benzothiazol-2-yl)-2H,5H-pyrano-[3,2,c][1]benzopyran-2,5-dione and 8-

(dimethylamino)-2,5-dioxo-2H,5H-pyrano[3,2,c][1]benzopyran-3-ethyl carboxylate can be mentioned.

As pyranoquinoline-2,5-dione derivatives e.g. 8-(dimethylamino)-3-phenyl-2H-pyrano[3,2,c]quinoline-2,5(6H)-dione, 6-methyl-3-(benzothiazol-2-yl)-2H-pyrano[3,2-c]quinoline-2,5-(6H)-dione and 8-(dimethylamino)-2H-pyrano[3,2-c] quinoline-2,5(6H)-dione-3-ethyl carboxylate can be used.

As pyrazole quinoxaline derivatives e.g. 7-(dimethylamino)-3-methyl-1-phenyl-1H-pyrazolo[3,4-b] quinoxaline and 7-(dimethylamino)-3-ethyl-1-phenyl-1H-pyrazolo[3,4-b]quinoxaline can be used.

Suitable 2-pyrano-isoquinoline-3,6-dione derivatives are e.g. 2-(2'-benzothiazolyl)-5-methyl-pyrano[2,3-c] isoquinoline-3,6-dione, 2-(2'-benzothiazolyl)-5-methyl-pyrano[2,3-c] isoquinoline-3,6-dione and 2-(2'-benzothiazolyl)-pyrano[2,3-c] isoquinoline-3,6-dione.

A usuable benzimidazo-benzisoquinolin-7-one derivative is e.g. 7H-benzimidazo[2,1-a]benz[de]-isoquinolin-7-one.

Acridine derivatives are e.g. 3,6-diamino-2,7-dimethylacridine hydrochloride, 3,6-diaminoacridine hydrochloride and 6,9-diamino-2-ethoxyacridine hydrochloride.

Other preferred fluorescent substances are: 2,2'-dihydroxy-1,1'-naphthalazine, 4-dimethylaminochalcone, 3-methoxybenzanthrone, the sodium salt of 6-amino-2,3-dihydro-1,3-dioxo-2-p-tolyl-1H-benz[de]isoquinoline-5-sulphonic acid, chlorotetracycline and/or N-salicylidene-4-dimethylaminoaniline.

The fluorescent substances used according to the invention prove to be advantageous particularly when incorporated in colorless or tooth-colored dental materials because they do not lead to any significant visible discoloration of the latter. According to the invention in particular spacer varnishes, blocking materials, sealant varnishes for prostheses, protective coatings for dentine, fissure sealants, composite filling materials such as molar material, synthetic cementing substances for crowns and inlays, and dental cements find application as dental materials. When choosing the dental material to be used in each case, however, regard should be paid to the fact that neither the dental material itself nor one of its components lead to a change in the fluorescent substance as a result of which the latter would possibly lose its capacity for fluorescence. The fluorescent substances used are compatible with many different dental materials and do not lose their capacity for fluorescence even when the dental material provided with them is exposed for a relatively long period to the chemical and physical effects which act on the natural teeth. Consequently, it is also not necessary, as it is with the known processes, to incorporate the fluorescent substances in microcapsules in order to achieve acceptable compatibility with the dental materials and a suitable chemical and physical stability.

In particular natural teeth, false teeth or parts thereof are provided for as substances to which the dental material comprising the fluorescent substance is applied.

In order that the fluorescent, preferably colorless or tooth-colored dental material can be distinguished in a simple manner from natural teeth, false teeth, parts thereof or other dental materials, or in order that it be more clearly visible, it is irradiated, after being applied to the substrate, with a light source emitting light of a wave length in the region of 360 to 480 nm and then viewed through a light filter filtering out at least partially, preferably essentially completely the light of a wave length in the region of 360 to 480 nm. In this way, the fluorescent substances present in the dental material according to the invention are excited to emit fluorescent light as a result of which the dental materials can be distinguished easily from the natural teeth or false teeth surrounding them. The interfering effects accepted with known processes caused by reflection of the exciting light and by the fluorescent light of natural teeth in the wave length range of 350 to 480 nm are overcome in a simple manner according to the invention by the fact that the interfering wave lengths of light are filtered out with a light filter for light with a wave length of 360 to 480 nm. It is particularly advantageous that the required light source and light filter are already available to the peersons normally dealing with dental materials, such as dental technicians or dentists, in the form of conventional blue light lamps with the aid of which, for example, fillings made of photopolymerizable synthetic material are cured, and common orange filters for protection against this blue light. Particularly preferred light sources are commerical blue light polymerization lamps and particularly preferred light filters are for example the light filters Plexiglas ® Orange 478 and Plexiglas ® Gelb 303 (sold by Röhm GmbH, Germany). There is thus no need to procure special UV light sources as is necessary for carrying out the known processes.

Although the dental materials according to the invention do not assume any appreciable color due to the fluorescent substances incorporated in them, they can be distinguished easily from the natural teeth or false teeth surrounding them as a result of the fluorescent light emitted on excitation in the wave length range of 480 to 600 nm, and they can thus be applied very accurately, excesses being clearly discernible. In preference, the process according to the invention and the dental materials according to the invention always find application when, for aesthetic considerations, dental materials are to be used which are colorless or tooth-colored at daylight but which can nevertheless be distinguished from natural teeth, false teeth, parts thereof and other dental materials, even over a relatively long time period.

The invention is illustrated in more detail in the following examples. EXAMPLE 1

Spacer varnish for stumps

Conventional spacer varnishes are strongly colored so that they can be applied accurately to a model stump. This color of the varnish is, however, troublesome after jacket crowns have been applied to the stump because the varnish shines through the crown and thus changes the color of the crown.

A spacer varnish was prepared by dissolving 50 g Elastosil ® E41 (Wacker, Germany) and 50 mg of the fluorescent substance 7-di-methyl-amino-4-trifluoromethyl coumarin in 60 g of toluene. The spacer varnish proved to be practically colorless by daylight even in thick layers. When irradiated with the blue light of a commercial polymerization lamp for light-curing composites and viewed through the light filter Plexiglas ® Orange 478 or Plexiglas ® Gelb 303 (Röhm, Germany) or also through commercial goggles for protection against polymerization light of the kind frequently used by dental technicians or dentists, the varnish itself could be distinguished by a luminous yellow-green color, even in thin layers.

EXAMPLE 2

Blocking material for blocking out undercuts in the case of models of dental preparations such as crown stumps or inlay cavities. Commercial blocking materials are usually intensively colored in order to permit exact application. This intensive color is, however, troublesome particularly in the case of inlays made of synthetic materials or ceramics and in the case of jacket crowns because it shines through the inlay or the crown when the work is completed and thus can lead to a color mismatch.

A blocking material was prepared by mixing equal parts of base paste and catalyst paste. The catalyst paste was prepared by dissolving 1.0 g dibenzoyl peroxide and 0.02 g hydroquinone in 40 g of triethylene glycol dimethacrylate and 60 g bisphenol A-diglycidylmethacrylate and kneading this solution in a mortar into 75 g silanized Aerosil ® OX50 (Degussa).

The associated base paste was prepared in a similar manner, but with 1.0 g N,N-diethanol-p-toluidine and 0.1 g of the fluorescent substance 7-dimethylamino-4-trifluoromethyl coumarin being used instead of dibenzoyl peroxide and hydroquinone. The pot life of the blocking material could be adjusted to a value of 3 to 4 minutes by adding dibenzoyl peroxide or hydroquinone.

The blocking material obtained in this way did not have an intensive color. Nevertheless, as described in Example 1, it could be made readily visible with the aid of a polymerization lamp and a filter, as a result of which very exact application was possible.

EXAMPLE 3

Sealant varnish for prostheses 5 mg of the fluorescent substance 3,9-perylene diisobutyl carboxylate were dissolved in a sealant varnish for prostheses composed of 50 g methylmethacrylate, 50 g dipentaerythritol monohydroxy pentaacrylate and 1.5 g Irgacure ® 651 (Ciba-Geigy).

The sealant varnish prepared in this way proved to be practically colorless. After the varnish had been applied to the prosthesis it could however, as described in Example 1, be made visible with the aid of a polymerization lamp and a filter. In this way, the varnish layer applied could be examined for defects and thin or uneven places, which was advantageous particularly in the case of poorly accessible places such as the interdental regions or the critical regions at the transition from tooth to prosthesis material. After this examination, the varnish was cured in a dental light polymerization apparatus.

EXAMPLE 4

Protective coating for dentine

A fluorescent protective coating for dentine was prepared by dissolving 15 mg of benzothioxanthene-3,4-dicarboxylic acid-N-stearylimide and 30 g Vinapas ® C-305 (Wacker GmbH) in 200 g of diethylketone.

As described in Example 1, the protective coating for dentine can be made visible with the aid of a polymerization lamp and a filter and can be distinguished easily from natural teeth and false teeth, as a result of which it can be applied to specific places and the entire application can be well controlled. By normal daylight, on the other hand, the protective coating for dentine cannot be distinguished from natural or false teeth.

EXAMPLE 5

Fissure sealant

Well known fissure sealants are usually strongly white-pigmented so that they can be distinguished clearly from the natural tooth. This is particularly advantageous during the application of the sealant and for subsequent checks. However, strongly white pigmented fissure sealants have the disadvantage that they stand out in an undesirable manner from the natural teeth in terms of color and light-curing products can be polymerized only in thin layers.

A fluorescent light-curing and tooth-colored fissure sealant was prepared by incorporating, with a dispersing apparatus, the quantities of titanium dioxide and iron oxide pigments required for the desired color in a monomer composition comprising 0.003 g 3,9-perylene diisobutylcarboxylate, 0.3 g camphor quinone, 0.5 g N,N-3,5-tetramethylaniline, 40 g triethyleneglycol dimeth-acrylate and 60 g bisphenol A-diglycidylether. All operations were carried out in a darkroom.

The tooth-colored fissure sealant obtained in this way could, as described in Example 1, be distinguished clearly from the natural tooth with the aid of a customary polymerization light lamp and a light filter by virtue of the emission of yellow-green fluorescent light.

EXAMPLE 6

Composite filling material

A monomer component was prepared by dissolving 0.5 g N,N-3,5-tetramethylaniline, 0.3 g 'amphor quinone and 0.1 g 7-dimethyl-amino-4-trifluoromethyl coumarin in a mixture of 60 g bisphenol A-diglycidyl ether and 40 g triethyleneglycol dimethacrylate. At the same time, a prepolymer was prepared by mixing 1 g dibenzoyl peroxide, 40 g silanized Aerosil ® OX50, 30 g dodecane diol dimethacrylate and 30 g of a trimethyl-hexamethylene diisocyanate dihydroxyethyl methacrylate adduct; the mixture was subjected to thermal polymerization at 120° C. for one hour and subsequently milled in a ball mill to an average particle size of 30 $\mu$m. For the preparation of the composite, initially 21 g silanized Aerosil ® OX50 (Degussa) and subsequently 50 g of the prepolymer were incorporated in 29 g of the monomer component prepared in a mortar. A composite in paste form with an acceptable consistency suitable for teeth stopping was obtained, the desired color of the composite being obtained by adding the necessary quantities of colored pigments. Apart from the preparation of the prepolymer, all the work was carried out in a darkroom.

The tooth-colored composite filling material obtained in this way could, in contrast to the known tooth-colored composite filling materials, be shown up in a contrasting color to the natural tooth, as described in Example 1. Edges projecting over the tooth were easy to recognize in this way and hence to remove.

EXAMPLE 7

Synthetic cementing material for crowns and inlays

Catalyst paste: A monomer component was prepared by dissolving 1.0 g dibenzoyl peroxide and 0.03 g hydroquinone in a mixture of 30 g triethyleneglycol dimethacrylate and 70 g of a tri-methyl-hexamethylene diisocyanate dihydroxyethyl methacrylate adduct. 40 g silanized Aerosil ® OX50 were stirred into 60 g of the monomer component A as a result of which a paste with a fluid consistency was obtained.

The base paste was prepared by dissolving 1.0 g N,N-3,5-tetra-methylaniline, 0.6 g camphor quinone and 0.08 g 7-dimethylamino-4-trifluoromethyl coumarin in a mixture of 30 g triethylene glycol dimethacrylate and 70 g of a trimethylhexamethylene diisocyanate-dihydroxyethyl methacrylate adduct. 40 g silanized Aerosil ® OX50 and the quantity of pigment required for coloring were stirred into 60 g of this monomer component. All the operations for preparing the base paste were carried out in a darkroom.

By mixing equal parts of base paste and catalyst paste, self-curing of the material was initiated, the pot life being 3 to 4 minutes. The material could also be polymerized by irradiation with polymerization light having a wave length of 400 to 500 nm.

The synthetic cementing material described proved to be tooth-colored by daylight. As described in Example 1 it could, however, be distinguished from the natural teeth and the crowns or inlays in order to remove any excess after the cementing of crowns and inlays.

We claim:

1. A method for the optical distinction of a dental material applied to a substrate from natural or false teeth which comprises the steps of:
   a) Incorporating into the dental material 0.00001 to 1% by weight of a fluorescent substance having an absorption maximum in the wave length range of 360 to 480 nm and a sluorescence maximum in the wave length range of 480 to 600 nm,
   b) Applying said dental material to said substrate,
   c) Irradiating said material with a light source emitting light of a wavelength in the region of 360 to 480 nm and
   d) viewing said material through a light filter filtering out at least partially the light wave in the region of 360 nm to 480 nm.

2. Dental material for use in the process according to claim 1 comprising coumarin derivatives, phthalimide derivatives, fluoranthene derivatives, perylene derivatives, xanthene derivatives, thioxanthene derivatives, pyrano-benzopyran-2,5-dione derivatives, pyrano-quinoline-2,5-derivatives, pyrazole quinoxaline derivatives, 2-pyrano-isoquinoline-3,6-dione derivatives, benzimidazo-benz-isoquinolin-7-one derivatives, acridine derivatives or mixtures of the above-mentioned derivatives as fluorescent substances.

3. Dental material according to claim 2 which comprises as coumarin derivative a compound selected from the group consisting of:
   7-dimethylamino-4-(trifluoromethyl) coumarin,
   7-amino-4-(trifluoromethyl) coumarin,
   7-(dimethylamino)-4-(trifluoromethyl) coumarin,
   7-(ethylamino)-6-methyl-4-(trifluoromethyl) coumarin,
   2,3,6,7-tetrahydro-9-(trifluoromethyl)-1H,5H,11H-[1] benzopyrano [6,7,8-ij]-quinolizin-11-one,
   6,7,8,9-tetrahydro-4-(trifluoromethyl)-2H-pyrano [3,2,-c]-quinolin-2-one,
   7-(diethylamino)-3-(1-methyl-1H-benzimidazol-2-yl)-2H-1-benzopyran-2-one,
   3-(2-benzimidazolyl)-7-(diethylamino) coumarin,
   10-acetyl-2,3,6,7-tetrahydro-1H,5H,11H-[1]benzopyrano [6,7,8-ij]quinolizin-11-one,
   3-(2-benzothiazolyl)-7-(diethylamino) coumarin,
   2,3,6,7-tetrahydro-11-oxo-1H,5H,11H-[1] benzopyrano [6,7,8-ij] quinolizine-10-carboxylic acid,
   2,3,6,7-tetrahydro-11-oxo-1H,5H,11H-[1] benzopyrano-[6,7,8-ij] quinolizine-10-ethyl carboxylate, as phthalimide derivative a compound selected from the group consisting of
   4-amino-N-methyl phthalimide,
   4-(dimethylamino)-N-methyl phthalimide and/or
   4-(2H-naphthol[1,2-d]triazol-2-yl)-N-methyl phthalimide, as fluoranthene derivative a compound selected from the group consisting of
   fluoranthene-2,3-dicarboxylic anhydride and
   1-methyl fluoranthene-2,3-dicarboxylic anhydride, as perylene derivative a compound selected from the group consisting of
   perylene and
   3,9-perylene diisobutyl dicarboxylate, as xanthene derivative 2,8-dimethylnaphtho[3,2,1-kl]xanthene, as thioxanthene derivative benzothioxanthene-3,4-dicarboxylic acid-N-stearylimide, as pyrano-benzopyran-2,5-dione derivative a compound selected from the group consisting of
   3-(benzothiazol-2-yl)-2H,5H-pyrano[3,2,c][1]benzopyran-2,5dione,
   3-benzimidazol-2-yl)-2H,5H-pyrano[3,2,c][1]benzopyran-2,5-dione,
   8-hydroxy-3-(benzimidazol-2-yl)-2H,5H-pyrano-[3,2,c] [1]benzopyran-2,5-dione,
   8-(dimethylamino)-3-phenyl-2H,5H-pyrano[3,2,c][1-]benzo-pyran-2,5-dione,
   8-(dimethylamino)-3-(benzothiazol-2-yl)-2H,5H-pyrano[3,2,c][1]benzopyran-2,5-dione and
   8-(dimethylamino)-2,5-dioxo-2H,5H-pyrano[3,2,c][1-]benzo-pyran-3-ethyl carboxylate, as pyranoquinoline-2,5-dione derivative a compound selected from the group consisting of
   8-(dimethylamino)-3-phenyl-2H-pyrano[3,2,c]-quinoline-2,5(6H)-dione,
   6-methyl-3-(benzothiazol-2-yl)-2H pyrano[3,2-c]quinoline-2,5-(6H)-dione and
   8-(dimethylamino)-2H-pyrano[3,2-c]quinoline-2,5-(6H)-dione-3-ethyl carboxylate, as pyrazole quinoxaline derivative a compound selected from the group consisting of
   7-(dimethylamino)-3-methyl-1-phenyl-1H-pyrazolo[3,4-b] quinoxaline and
   7-(dimethylamino)-3-ethyl-1-phenyl-1H-pyrazolo[3,4-b] quinoxaline, as 2-pyrano-isoquinoline-3,6-dione derivative a compound selected from the group consisting of
   2-(2'-benzothiazolyl)-5-methyl-pyrano[2,3-c] isoquinoline-3,6-dione,
   2-(2'-benzothiazolyl)-5-methyl-pyrano[2,3-c] isoquinoline-3,6-dione and
   2-(2'-benzothiazolyl)-pyrano[2,3-c] isoquinoline-3,6-dione, as benzimidazo-benzisoquinolin-7-one derivative a compound selected from the group comprising
   7H-benzimidazo[2,1-a]benz[de]-isoquinolin-7-one and as acridine derivative a compound selected from the group consisting of
   3,6-diamino-2,7-dimethylacridine hydrochloride,
   3,6-diaminoacridine hydrochloride and
   6,9-diamino-2-ethoxyacridine hydrochloride.

4. Dental material for use in the process according to claim 1 comprising as fluorescent substance a compound selected from the group consisting of
2,2'-dihydroxy-1,1'-naphthalazine,
4-dimethyl-aminochalcone,
3-methoxybenzanthrone,
the sodium salt of 6-amino-2,3-dihydro-1,3-dioxo-2-p-tolyl-1H-benz[de]isoquinoline-5-sulphonic acid,
chlorotetracyclin and
N-salicylidene-4-dimethylaminoaniline.

* * * * *